(12) United States Patent
Tsimikas et al.

(10) Patent No.: US 6,375,925 B1
(45) Date of Patent: Apr. 23, 2002

(54) METHODS AND REAGENTS FOR NON-INVASIVE IMAGING OF ATHEROSCLEROTIC PLAQUE

(75) Inventors: Sotorios Tsimikas; Joseph L. Witztum; Wulf Palinski; Linda K. Curtis, all of San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/381,594
(22) PCT Filed: Nov. 8, 1996
(86) PCT No.: PCT/US96/18289
   § 371 Date: Nov. 22, 1999
   § 102(e) Date: Nov. 22, 1999
(87) PCT Pub. No.: WO98/21581
   PCT Pub. Date: May 22, 1998
(51) Int. Cl.[7] .......................... A61K 51/00; A61B 5/055
(52) U.S. Cl. ...................................... 424/1.49; 424/9.34
(58) Field of Search ............................... 424/1.49, 4.69, 424/9.34, 9.36, 178.1, 179.1; 514/824; 530/391.1, 391.3

(56) References Cited

U.S. PATENT DOCUMENTS 5,364,612 A * 11/1994 Goldenberg ............... 424/1.53

FOREIGN PATENT DOCUMENTS

WO    WO91/02252    *  2/1991  ......... G01N/33/567

OTHER PUBLICATIONS

Palinski et al., "Antisera and monoclonal antibodies specific for epitopes generated during oxidative modificationof low density lipoprotein," Arteriosclerosis 10:325–335, May 1990.*

* cited by examiner

*Primary Examiner*—Michael G. Hartley
(74) *Attorney, Agent, or Firm*—Foley & Lardner

(57) ABSTRACT

The invention provides reagents and methods for their use in in vivo diagnosis of atherosclerosis. In particular, the invention provides monoclonal antibodies which bind oxidation specific epitopes in atherosclerotic plaque lesions, such as those which occur in oxidized LDL, in vivo with high binding specificity; i.e., at about 10 to 20 times the rate of binding of the antibodies to adjacent normal arterial tissue. When detectably labeled and administered according to the invention, the antibodies are clearly imaged when bound to atherosclerotic plaque using known imaging techniques and devices, such as a gamma camera. In addition, the invention provides a method for substantially reducing interference from background signal in the blood pool into which such agents are introduced for detection and quantification of atherosclerotic plaque burden in the cardiovascular tissue of a host.

12 Claims, 10 Drawing Sheets

METHODS AND REAGENTS FOR NON-INVASIVE IMAGING OF ATHEROSCLEROTIC PLAQUE

STATEMENT AS TO FEDERALLY SPONSORED RESEARCH

This invention was made with government support under Grant No. 5T32HL07444-15 awarded by The National Institutes of Health. The government has certain rights in the invention.

This application is a 371 of PCT/US96/18289, filed Nov. 8, 1996.

FIELD OF THE INVENTION

This invention relates to the diagnosis of atherosclerosis. Specifically, the invention relates to methods and reagents for imaging atherosclerotic plaque in vivo.

HISTORY OF THE INVENTION

Clinical diagnosis of atherosclerosis is typically based (together with patient history and physical examination) on the results of an invasive diagnostic procedure such as angiography. A major impediment to the development of non-invasive diagnostic methods for atherosclerosis has been the lack of reagents and techniques which can distinguish plaque from components of normal vessel walls and blood. Reagents which have been investigated for binding to atherosclerotic plaque components include radiolabeled lipoprotein (LDL), apolipoprotein B (apo B), autologous platelets, antifibrin antibodies and components related to smooth muscle cell proliferation. In general, however, such agents have suffered from a lack of specificity and their detection in vivo has been complicated by substantial residual background signal which interferes with resolution of the target image.

SUMMARY OF THE INVENTION

The invention provides reagents and methods for their use in in vivo diagnosis of atherosclerosis. In particular, the invention provides monoclonal antibodies which bind oxidation-specific epitopes of oxidized LDL in vivo in atherosclerotic plaque lesions with high binding specificity. In addition, the invention provides a method for substantially reducing interference from background signal in the blood pool into which such agents are introduced for detection and quantification of atherosclerotic plaque burden.

An example of the monoclonal antibodies provided by the invention is MDA2, a murine IgG1α antibody which has been discovered to have unpredictably high binding specificity in vivo for malondialdehyde (MDA)-lysine epitopes on oxLDL (particularly in the oxLDL-rich apoB component of atherosclerotic plaque). According to the diagnostic method of the invention, detectably labeled MDA2 monoclonal antibodies or Fab fragments thereof are introduced into the bloodstream of a patient. Detection of MDA2 bound to an atherosclerotic plaque lesion may be made by any method appropriate to the label applied to MDA2, but use of gamma and positron emitters for ease of signal detection and quantification of plaque burden based thereon is preferred.

MDA2 is taken up by atherosclerotic plaque at a rate of up to about 20 times higher than its rate of uptake by adjacent arterial tissue, where no detectable binding of MDA2 is found. MDA2 does not bind unoxidized LDL. A particular advantage of the invention is that by targeting the oxLDL-rich regions of atherosclerotic plaque, "hot spots" in plaque believed to be clinically relevant markers for unstable plaque lesions may be clearly imaged by detection of MDA2 binding in such lesions.

A further example of the monoclonal antibodies of the invention is NA59, a murine IgG1α antibody which has also been discovered to have unusually high binding specificity in vivo for atherosclerotic plaque, in particular for 4-hydroxynonenal (4-HNE)-lysine epitopes in oxLDL. The NA59 mAb and Fab fragments thereof are taken up by atherosclerotic plaque at rates similar to MDA2 and are suitable for use as an in vivo diagnostic agent in the same manner described with respect to MDA2.

According to the diagnostic method of the invention, detectably labeled oxidation-specific antibodies such as MDA2 or NA59 are introduced into the bloodstream of the patient. To clear residual background signal, MDA or 4-HNE antigen (preferably joined to a carrier such as albumin or LDL) is also introduced into the bloodstream of the patient. On injection of the modified antigen, unbound MDA2 levels in circulation decline rapidly and most of the background signal is eliminated.

Binding of the monoclonal antibodies of the invention to oxLDL epitopes in atherosclerotic plaque is detected as noted above. The percent of the injected dose of either antibody taken up by plaque in vivo correlates strongly with the amount of plaque present in the imaged tissue, which may be estimated from the results of the inventive diagnostic assay.

DESCRIPTION OF THE PREFERRED EMBODIMENTS

Figure 1:
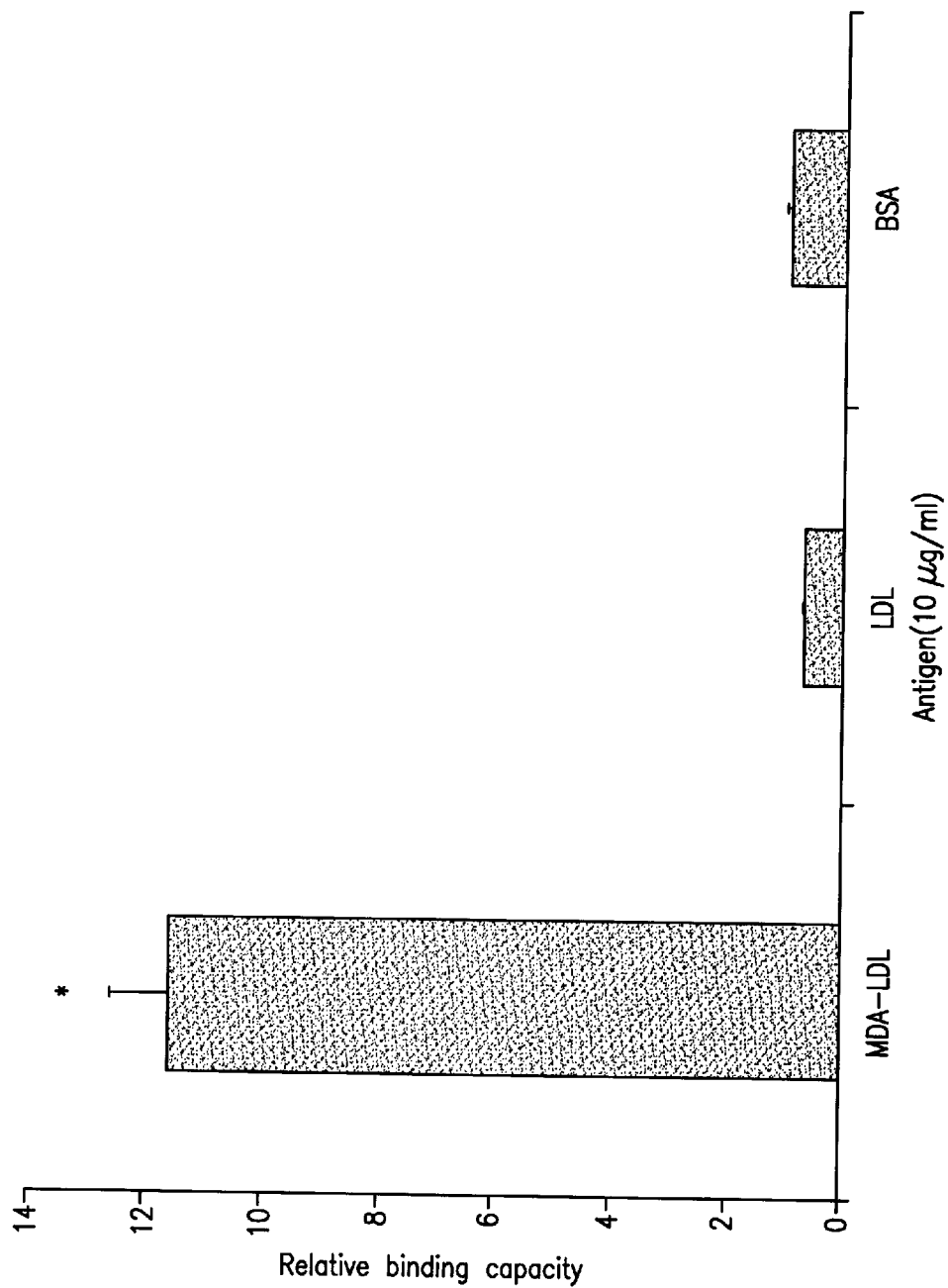
FIG. 1 is a graph of data showing in vitro binding (determined by radioimmunoassay) of iodinated MDA2 antibody to MDA-LDL in preference to LDL, demonstrating that binding specificity was not lost by radiolabeling the antibody. Bovine serum albumin (BSA) is the control.

The preferred embodiments of the invention are described below. All publications mentioned herein are incorporated herein by reference to illustrate known methods and/or materials which may be of use in, but not essential to, the practice of the invention.

A. Definitions

The invention may be more readily understood with reference to definitions commonly used by those of ordinary skill in the art for many of the technical terms used in this disclosure. Unless otherwise noted, all technical terms used herein have the same meaning as commonly understood by one of ordinary skill in the art to which this invention belongs.

1. The term "antibody" as used in this disclosure is meant to include intact molecules as well as fragments thereof, such as for example, Fab and F(ab')2, which are capable of binding an oxLDL epitopic determinant. The term "human antibody" means an antibody in which portions of the immunoglobulin molecule are encoded by a DNA sequence derived from a human Ig-encoding nucleic acid sequence. Such human antibodies are desirable for use in antibody therapies, as such antibodies would elicit little or no immune response in a human patient. Preferably, the human antibody is entirely human, however, "humanized" antibodies are also envisioned.

2. "Antibody fragments" retain some ability to selectively bind with its antigen or receptor and are defined as follows:

(a) Fab, the fragment which contains a monovalent antigen-binding fragment of an antibody molecule can be produced by digestion of whole antibody with the enzyme papain to yield an intact light chain and a portion of one heavy chain;

(b) Fab', the fragment of an antibody molecule can be obtained by treating whole antibody with pepsin, followed by reduction, to yield an intact light chain and a portion of the heavy chain. Two Fab' fragments are obtained per antibody molecule;

(c) (Fab')2, the fragment of the antibody that can be obtained by treating whole antibody with the enzyme pepsin without subsequent reduction. F(ab')2 is a dimer of two Fab' fragments held together by two disulfide bonds;

(d) Fv, defined as a genetically engineered fragment containing the variable region of the light chain and the variable region of the heavy chain expressed as two chains; and (e) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, Antibodies: A Laboratory Manual, Cold Spring Harbor Laboratory, New York (1988), incorporated herein by reference).

3. By the term "binding specificity" is meant the ability of an antibody to recognize and bind a specific antigenic epitope. A highly specific antibody binds its antigenic epitope with a high affinity, e.g., an enhanced binding affinity.

4. As used herein, the term "chimeric antibody" refers to an antibody in which the variable regions of antibodies derived from one species are combined with the constant regions of antibodies derived from a different species or alternatively refers to complementary determining region grafted antibodies. "CDR" or "complementarity determining region" or "hypervariable region" is defined as the amino acid sequences on the light and heavy chains of an antibody which form the three-dimensional loop structure that contributes to the formation of the antigen binding site. As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

B. Antibodies for Use in Imaging Atherosclerotic Plaque

The present invention provides methods and reagents for in vivo use which specifically target oxidation-specific epitopes, such as those occuring in oxidatively modified LDL, in atherosclerotic plaque lesions. Such epitopes are generated in vivo by the peroxidation of polyunsaturated fatty acids that release aldehydes (such as MDA and 4-HNE), which subsequently attach by covalent bonds to lysine residues on apoB-forming oxLDL, as well as by oxidation of phospholipids. Malondialdehyde (MDA)-lysine and 4-hydroxynonenal (4-HNE)-lysine are examples of such epitopes. Other lysine-oxLDL epitopes are known to those of ordinary skill in the art; e.g., 4-hydroxyhexenal (4-HHE)-lysine, 4-hydroxyoctenal (4-HOE)-lysine, 2,4-heptadienal-lysine.

Oxidation-specific epitopes in oxLDL are particularly attractive targets for imaging according to the invention. OxLDL becomes incorporated into plaque lesions during atherogenesis when excess plasma LDL enters the arterial wall at lesion-prone areas and becomes oxidatively modified by various cell types (e.g., endothelial cells, macrophages and fibroblasts). Resident macrophages take up oxLDL, resulting in the foam cell formation which characterizes the lesions formed in the early stages of atherogenesis. Over time, the foam cells are degraded, releasing lipids into the extracellular space where an atheroma forms. Atherosclerotic plaque grows by, in part, incorporating and oxidizing additional lipoprotein. Thus, oxLDL is a significant marker for the existence of, and growth in, atherosclerotic plaque.

The monoclonal antibodies of the invention are immunoreactive with and bind to oxidation-specific epitopes in atherosclerotic plaque lesions in vivo. The monoclonal antibodies useful in the invention will be those which have a binding specificity for such oxidation specific epitopes which is comparable to the unexpectedly high binding specificities of MDA2 and NA59. Specifically, the monoclonal antibodies of the invention bind oxidation specific epitopes such as those in oxLDL at a rate of up to 20 times the rate of binding to normal arterial tissue, preferably at a rate of 10–20 times the rate of binding to normal arterial tissue. Such antibodies do not bind unoxidized LDL. All such monoclonal antibodies may be prepared using techniques familiar to those of ordinary skill in the art as described below.

As described in Example I, the MDA2 and NA59 antibodies were developed to target known aldehyde-lysine epitopes in oxidatively modified LDL; i.e., malondialdehyde (MDA)-lysine and 4-hydroxynonenal (4-HNE)-lysine, respectively. Although oxLDL epitopes are natural targets for detection of atherosclerotic plaque, candidate epitope binding agents must, to be useful in imaging plaque, bind the epitopes in plaque specifically (to the exclusion of other epitopes elsewhere), be susceptible to detectable labeling (without destroying the binding characteristics of the agent) and be taken up to an extent and at a rate sufficient to permit imaging of a substantial area of plaque (to permit quantification of plaque burden). In vitro binding patterns of agents not identical or equivalent to agents tested in vivo are not accurately predictive of whether an untested binding candidate will possess these necessary characteristics when used in vivo.

Both MDA2 and NA59 bind oxLDL epitopes in plaque with unexpectedly high binding specificity (to the exclusion of other epitopes elsewhere), may be detectably labeled without loss of binding specificity and are taken up in atherosclerotic plaque in vivo to an extent and at a rate sufficient to permit imaging of a substantial area of the plaque burden. Specifically, as illustrated in Example V, binding of MDA2 within plaque in an animal model of atherosclerosis occurred about 12.6 to nearly 20 times as often as nonspecific binding to adjacent normal arterial tissue. NA59 is also directed to a lysine-based oxLDL epitope and demonstrates binding characteristics which are almost identical to those of MDA2 . Fab and (Fab')2 fragments of the monoclonal antibodies of the invention bind oxidation specific epitopes in plaque in vivo with similar binding specificity. Thus, MDA2 and NA59 bind to lysine-based oxLDL epitopes in plaque with sufficient specificity to distinguish, by detection of bound antibody, plaque from surrounding blood and normal tissue.

Specific techniques for generating monoclonal antibodies with the binding specificities of MDA2 and NA59 are described in Example I. In general, techniques for making monoclonal antibodies are known and may be readily employed by those of ordinary skill in the art to generate monoclonal antibodies having the characteristics taught herein.

Such antibodies can be prepared using an intact polypeptide or fragments containing the peptides of interest as the immunizing antigen; e.g., malondialdehyde (MDA) and 4-hydroxynonenal (4-HNE), 4-hydroxyhexenal (4-HHE) or 4-hydroxyoctenal (4-HOE), conjugated to lysine residues of peptides of apoB or LDL. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid, as well as similarly modified homologous proteins. The coupled peptide is then used to immunize the animal (e.g., a mouse or a rabbit).

Hybridomas prepared from spleen cells of an immunized animal which secrete a desired monoclonal antibody can be produced in various ways using techniques well understood by those having ordinary skill in the art and will not be repeated in detail here. Details of these techniques are described in such references as *Monoclonal Antibodies-Hybridomas: A New Dimension in Biological Analysis,* edited by Roger H. Kennett, et al., Plenum Press, 1980; and U.S. Pat. No. 4,172,124, incorporated herein by reference.

Methods are also known in the art which allow antibody exhibiting binding for a preselected ligand to be identified and isolated from antibody expression libraries. For example, a method for the identification and isolation of an antibody binding domain which exhibits binding with a peptide of the invention is the bacteriophage λ vector system. This vector system has been used to express a combinatorial library of Fab fragments from the mouse antibody repertoire in *Escherichia coli* (Huse, et al., *Science,* 246:1275–1281, 1989) and from the human antibody repertoire (Mullinax, et al., *Proc. Natl. Acad. Sci.,* 87:8095–8099, 1990). As described therein, antibody exhibiting binding for a preselected ligand were identified and isolated from these antibody expression libraries. In particular, use of a murine library obtained from the ApoE-deficient mouse would yield a greatly enriched population of desired antibody binding domains because such mice spontaneously produce very high titers of autoantibodies to oxidation specific epitopes. This methodology can be applied to hybridoma cell lines expressing monoclonal antibodies with binding for a preselected ligand.

In addition, methods of producing chimeric antibody molecules with various combinations of "humanized" antibodies are known in the art and include combining murine variable regions with human constant regions (Cabily, et al. *Proc. Natl. Acad. Sci. USA,* 81:3273, 1984), or by grafting the murine-antibody complementary determining regions (CDRs) onto the human framework (Riechmann, et al., *Nature* 332:323, 1988). This invention therefore further provides chimeric antibodies of the peptide-specific antibodies described above or biologically active fragments thereof or use in the inventive method. Chimeric antibodies are constructed by recombinant DNA technology, and are described in, for example, Shaw, et al., *J. Immun.,* 138:4534 (1987), Sun, L. K., et al., *Proc. Natl. Acad. Sci. USA,* 84:214–218 (1987).

Briefly, any of the above described antibodies or biologically active antibody fragments can be used to generate CDR grafted and chimeric antibodies. The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., *Antibody Engineering: A Practical Guide,* W. H. Freeman and Company, New York, 1992, incorporated by reference).

Also, under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared secondarily, from a parental hybridoma secreting monoclonal antibody of different isotype, by using the sib selection technique to isolate class-switch variants (Steplewski, et al., *Proc. Natl. Acad. Sci. U.S.A.,* 82:8653, 1985; Spira, et al., *J. Immunol. Methods,* 74:307, 1984). Thus, the monoclonal antibodies of the invention would include class-switch variants having binding specificity comparable to that of MDA2 and NA59 .

Cell lines which produce monoclonal antibodies are useful as ready sources of such antibodies. The isolation of cell lines producing monoclonal antibodies of the invention can be accomplished using routine screening techniques which permit determination of the elementary reaction pattern of the monoclonal antibody of interest. Thus, if a monoclonal antibody being tested binds a specific peptide, for example binds malondialdehyde (MDA)-lysine, then the monoclonal antibody being tested and the monoclonal antibody produced by the cell lines of the invention are equivalent.

It is also possible to determine, without undue experimentation, if a monoclonal antibody has the same specificity as a monoclonal antibody of the invention by ascertaining whether the former prevents the latter from binding to the peptide. If the monoclonal antibody being tested competes with the monoclonal antibody of the invention, as shown by a decrease in binding by the monoclonal antibody of the invention, then the two monoclonal antibodies bind to the same, or a closely related, epitope.

Still another way to determine whether a monoclonal antibody has the specificity of a monoclonal antibody of the invention is to pre-incubate the monoclonal antibody being tested with the peptide to which the antibody is presumed to be reactive, and then add the monoclonal antibody of the invention to determine if the monoclonal antibody of the invention is inhibited in its ability to bind the peptide. If the monoclonal antibody of the invention is inhibited then, in all likelihood, the monoclonal antibody being tested has the same, or functionally equivalent, epitopic specificity as the monoclonal antibody of the invention.

By using the monoclonal antibodies of the invention, it is possible to produce anti-idiotypic antibodies which can be used to screen monoclonal antibodies to identify whether the antibody has the same binding specificity as a monoclonal antibody of the invention. These antibodies can also be used for immunization purposes (Herlyn, et al., *Science*, 232:100, 1986). Such anti-idiotypic antibodies can be produced using well-known hybridoma techniques (Kohler and Milstein, *Nature*, 256:495, 1975). An anti-idiotypic antibody is an antibody which recognizes unique determinants present on the monoclonal antibody produced by the cell line of interest. These determinants are located in the hypervariable region of the antibody. It is this region (paratope) which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for a monoclonal antibody of the invention produced by a cell line which was used to immunize the second animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

The monoclonal antibodies of the invention are suited for use in vitro, for example, in immunoassays in which they can be utilized in liquid phase or bound to a solid phase carrier. The antibodies may be useful for monitoring the level of oxLDL in a tissue sample. Similarly, anti-idiotype antibodies are useful for measuring the level of oxLDL in a tissue sample. In addition, the monoclonal antibodies in these immunoassays can be detectably labeled in various ways. Examples of types of immunoassays which can utilize monoclonal antibodies of the invention are competitive and non-competitive immunoassays in either a direct or indirect format.

Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on tissue samples. Those of skill in the art will know, or can readily discern, other immunoassay formats without undue experimentation.

For use in vivo or in vitro, the monoclonal antibodies of the invention can be bound to many different carriers and used to detect the presence of oxLDL in vitro or in vivo. Examples of suitable carriers include, for in vivo use, proteins (e.g., BSA and lysine) and, for in vitro use, glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

For in vivo administration, the detectably labeled antibodies will preferably be formulated in a pharmaceutically acceptable carrier, most preferably a liquid (see, standard reference Remington's Pharmaceutical Sciences, which is incorporated herein by reference to illustrate knowledge in the art concerning suitable pharmaceutical carriers). Exemplary liquid carriers are saline, Ringer's solution, syrup, peanut oil, olive oil and like emulsions. The formulation can be in the form of an aqueous or nonaqueous liquid suspension and may include pharmaceutically acceptable preservatives.

In addition, the materials for use in the method of the invention are ideally suited for the preparation of a diagnostic kit. Kits useful in the claimed method comprise container means (such as vials, tubes, bottles, and the like) as well as means (such as a sterile syringe) for administering the contents of the container to a host. The syringe may be provided already loaded with a single dose of the detectably labeled antibody, or the antibody and/or a pharmaceutically acceptable carrier may be provided mixed or separated in one or more containers. Appropriate instructions regarding the safe use of the detectably labeled antibodies of the invention will be provided on the container labels or in a separate instruction sheet.

B. Method for In Vivo Diagnosis of Atherosclerosis

To use the monoclonal antibodies of the invention for the in vivo detection of plaque, the detectably labeled monoclonal antibody is given in a dose which is diagnostically effective. The term "diagnostically effective" means that the amount of detectably labeled monoclonal antibody is administered in sufficient quantity to enable detection of cardiovascular sites having plaque lesions. Further, it is desirable that the detectably labeled monoclonal antibody be rapidly cleared from the circulatory system in order to give the best target-to-background signal ratio.

Imaging post-injection is preferably made (as described further in Section C below) immediately following to about 24 hours after injection of the antibody, depending on the half-life of the radiolabel used and condition of the patient. Increased binding of detectably labeled antibody relative to a control (e.g., data evidencing the binding characteristics of the antibody to normal tissue) is indicative of the presence of atherosclerotic plaque in host cardiovascular tissue.

As a rule, the dosage of detectably labeled monoclonal antibody for in vivo diagnosis will vary depending on such factors as age, sex, and extent of disease of the individual. The dosage of monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

The dosage of radioisotope label required to detect oxLDL in atherosclerotic plaque in a host will also vary with the radioactivity of the radioisotope and will be taken into account in determining a suitable dose to be given of an imaging antibody according to the invention. For example, the mean lethal dosages of both $^{125}$I and $^{123}$I have been calculated at about 79+/-9 cGy (in Chinese hamster ovary cells; see, e.g., Makrigiorgos, et al., *Radiat.Res.*, 118:532–544). For diagnostic purposes, the dosage will be less than the mean lethal dose for the radioisotope.

For example, with respect to the half-life of common radioisotopes, the half-life of $^{123}$I at a dose between 1 and 20 microCi (mCi) is about 13 hours, while the half-life of $^{131}$I at a dose of less than 5 mCi is about 8 days. With respect to positron emitters, the half-life of $^{11}$C at a dose of 200 mCi or more is only 20 minutes, while the half-life of $^{18}$F at a dose of only 50 mCi is nearly six times as long. For example, it is expected that a useful dose of $^{123}$I-labeled antibody would be between 1 and 20 mCi, while less than 5 mCi of the longer-lived $^{131}$I would be used (e.g. 0.5–5 mCi) and approximately 200 mCi $^{11}$C can be used (e.g., 100–300 mCi). Thus, for use according to the invention, the preferred dose of agents including radioisotopes with longer half-lives will be less than the preferred dose of agents including radioisotopes with shorter half-lives.

One of ordinary skill in nuclear medicine would know to take the above and other salient characteristics of the radioisotopes into account when calculating an appropriate dosage. As a general matter, it is expected that a useful dose of detectably labeled antibody would deliver between about 0.5 and about 500 millicuries (mCi). In general, this dosage range will not vary substantially with the weight, age and sex of the host. However, in juvenile hosts, dosages in the lower spectrum of each preferred dosage range will be preferred, in order to limit accumulation of radioactivity in dividing cells.

Selection and modification of particular doses for each detectably labeled monoclonal antibody to be used in the invention is within the ordinary level of skill in the art. In particular, dosimetry calculations are well-known in the art which permit estimation of the distribution and radioactive burden to host tissues and cells on administration of radioisotopes. For review in this regard, those of skill in the art may wish to consult Makrigiorgos, et al., *J. Nucl. Med.*, 31:1358–1363, 1990, the disclosure of which is incorporated herein by this reference to illustrate knowledge in the art concerning dosimetric calculations of radioactivity distribution. Suitable animal models of atherosclerosis for use in evaluating the characteristics and efficacy of particular pharmaceutical agents are described in Example II.

The detectably labeled monoclonal antibodies of the invention will be administered by a parenteral route selected to best target the suspected site of plaque formation; i.e., intravascular or intra-arterial injection. Antigen administered to enhance clearance of residual radioactivity in background (blood) will be administered by the same routes utilized to administer the antibody.

The percent injected dose/gram (%ID/gm) aortic weight of the antibodies of the invention correlates strongly to the plaque burden (by weight) present in the cardiovascular tissue of the injected host. For example, as discussed in Example VII, there was a correlation of r=0.98 (98% accuracy) between %ID (not normalized for aortic weight) in plaque affected rabbits injected with MDA2 with total aortic weight and a similarly high correlation for plaque weight with %ID/gm (aortic weight normalized) rabbit injected with MDA2 . These data indicate that not only may plaque density be estimated from a standard curve of %ID/gm versus aortic weight generated by in vivo and in vitro control data obtained using the method of the invention, but also that oxLDL epitope density apparently increases with an increase in plaque burden. Because oxLDL is a clinical indicator of instability in atherosclerotic plaque, comparative data obtained from imaging antibody binding to oxLDL epitopes according to the invention in patients at different time points will assist clinicians in evaluating the clinical status and prognosis of the patient over time (in conjunction with other clinical signs, such as overall health, LDL serum levels and the like, all of which signs are known to those of ordinary skill in the art).

Thus, for monitoring the course of atherogenesis in a host as well as the host's responsiveness to therapy, the site of plaque formation may be imaged according to the invention more than once. Clearance of any previously administered radioactive agents (including those of the invention and chemotherapeutic agents) should be considered to limit detection of residual radioactivity. Rates of clearance may be determined based on known clearance rates for the particular radioisotopes present, or may be inferred by reimaging the host prior to readministering a detectably labeled monoclonal antibody according to the invention. Accumulation of the detectably labeled monoclonal antibodies of the invention in background will also be taken into account in this regard to maximize the target-to-background radioactivity ratios achieved in each imaging session.

Protocols and formulas for use in determining target-to-background ratios for radioactivity are well-known in the art. Depending on the radioisotope present, the detectably labeled monoclonal antibody may accumulate to some degree in tissues adjacent or distant from target tissues. Preferably, where possible, detectably labeled monoclonal antibodies will be chosen which do not accumulate at high levels in background tissues adjacent to suspected or known lesions of plaque formation (as compared to accumulation of the agent in more distant background tissues). Nonspecific binding of the detectably labeled antibodies of the invention is minimized by the high binding specificity of the antibodies for target oxLDL epitopes in atherosclerotic plaque. In addition, a method for enhancing detection of accumulation of the agent in target tissue is provided by the invention.

Specifically, a particularly advantageous aspect of the method of the invention is the technique it provides for reducing residual radioactivity in the background (i.e., blood) without interfering with antibody binding to target plaque. According to this aspect of the invention, the epitope antigen of the monoclonal antibody imaging agent (e.g., MDA or HNE) is coupled to a protein carrier (e.g., albumin or lysine) and injected into the bloodstream of the patient after injection of the imaging antibody. The time lapse between injection of the imaging antibody and injection of the antigen will vary depending on the time following injection when images are to be obtained, but will preferably be performed at least an hour following injection of the antigen to maximize removal of residular imaging antibody from plasma.

As discussed in Example VI, within two hours of injection of the antigen in WHHL rabbits previously injected with iodinated MDA2, residual radioactivity in the rabbit bloodstream was reduced by four-fold as compared to control rabbits which did not receive the antigen injection. The imaging index (target-to-background) in the antigen injected animals was substantially increased (from a ratio of about 0.6 in control animals to 1.3 in antigen injected animals). Thus, this aspect of the invention substantially enhances the target-to-background ratio for detection of antibody binding to plaque according to the invention.

C. Labeling of Monoclonal Antibodies for In Vivo Imaging of Atherosclerotic Plaque In vivo diagnostic imaging according to the invention is performed using oxLDL monoclonal antibodies as described above which have been detectably labeled; i.e., joined to a radioisotope whose presence in the body may be identified using a detection instrument. Those of ordinary skill in the art will be familiar with, or can readily ascertain the identity of, techniques and instruments for in vivo detection of radioactivity provided in the host by detachably labeled monoclonal antibodies used according to the invention.

To detect radioactivity provided by gamma emitter detectably labeled monoclonal antibodies, an instrument commonly known as a gamma camera (i.e., a system of scintillation crystals or photo multiplier tubes for analysis of radioactive decay) will be used to detect gamma emission from the detectably labeled monoclonal antibody. To detect radioactivity provided by positron emitter detectably labeled monoclonal antibodies, techniques and instruments for positron emission tomography (PET) and single photon positron emission spectography (SPECT) are available to, and well-known in, the art. Those of ordinary skill in the art will also recognize that the monoclonal antibodies of the invention may be coupled to paramagnetic isotopes for use in magnetic resonance imaging (MRI), may be coupled to paramagnetic isotopes for use in electron spin resonance (ESR) or may be covalently attached to contrast media for use in ultrasound. In general, any conventional method for visualizing diagnostic imaging can be utilized.

The selection of a detectably labeled monoclonal antibody and detection technique suitable for a given application is within the ordinary level of skill in the art. Factors to be considered in this respect include the existence of any host sensitivity to a particular radioisotope, in vivo toxicity and efficiency of such molecules, potential pharmaceutical interactions between the detectably labeled monoclonal antibody and other medications taken by the host, the availability of particular detection instruments, and cost of materials.

Thus, for in vivo diagnostic imaging, the type of detection instrument available is a major factor in selecting a given labeling agent. For radioactive labeling agents, the radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylene triaminepentacetic acid (DTPA) and ethylenediaminetetraacetic acid (EDTA) and similar molecules.

Typical examples of radioisotopes which can be bound to the monoclonal antibodies of the invention are $^{111}$In, $^{97}$Ru, $^{67}$Ga, $^{68}$Ga, $^{72}$As, $^{89}$Zr, $^{90}$Y, $^{201}$Tl, $^{157}$Gd, $^{55}$Mn, $^{162}$Dy, $^{52}$Cr, $^{56}$Fe, $^{122}$I, $^{123}$I, $^{124}$I, $^{125}$I, $^{126}$I, $^{131}$I, $^{80m}$Br, $^{82}$Br, $^{75}$Br, $^{76}$Br, $^{77}$Br, $^{80}$Br, $^{18}$Fl, $^{11}$C, $^{13}$N and $^{99m}$technetium. Particularly preferred for their safety and relative ease of use and detection are $^{111}$In and $^{99m}$technetium.

Those of ordinary skill in the art will be familiar with, or can readily ascertain, synthesis methods appropriate to the preparation of radioisotopically labeled monoclonal antibodies for use in the inventive method. For example, other suitable radioiodination labeling techniques are taught in Keough, et al, *J. Labeled Compound Radiopharm.*, 14:83–90, 1978. In addition, techniques useful in labeling molecules with positron emitters (e.g., $^{18}$fluorine) are known in the art and include the technique disclosed in Ishiwata, et al., *Eur. J. Nucl. Med.*, 9:185–189, 1984 ($^{18}$fluorine labeling of deoxyuridine). Techniques for labeling with non-halogen radioisotopes (such as $^{11}$C) are also well-known and include the technique referred to in Kubota, et al., *Jpn. J. Cancer Res.*, 80:778–782, 1989.

For in vitro use, there are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Examples illustrating practice of the method of the invention are set forth below. These examples should not, however, be considered to limit the scope of the invention, which is defined by the appended claims. In the examples, the abbreviation "min." refers to minutes, "hrs" and "h" refer to hours, "i.v." refers to intravenous, "mAb" refers to monoclonal antibody, and measurement units (such as "ml") are referred to by standard abbreviations.

EXAMPLE I

Preparation of MDA2 and NA59 Monoclonal Antibodies

BALB/c mice were immunized with 60 µg of malondialdehyde (MDA)-lysine modified murine LDL or 4-hydroxynonenal (4-HNE)-lysine modified murine LDL in 0.3 mL of phosphate buffered saline four times over a 6 week period. Fusions were performed with a myeloma cell line using conventional hybridoma construction techniques. Hybridoma supernatants were screened after 14 days using oxLDL, malondialdehyde (MDA) and 4-hydroxynonenal (4-HNE) as the antigens and selected hybridomas cloned. The murine immunoglobulin class of the antibodies was identified using a commercially available kit.

For use as a control antibody in in vivo experimentation, a commercially available IgG1α murine monoclonal antibody to human albumin (Halb) was obtained from Pierce Chemical.

EXAMPLE II

Antibody Radiolabeling

Iodination. MDA2, NA59 and Halb were iodinated with the known lactoperoxidase/glucose oxidase method using a commercial kit (Enzymobead Radioiodination Reagent, BIORAD). Briefly, 200 µg cold antibody in 50 µl PBS was added to 200 µl 0.2M phosphate buffer (pH 7.2), 50 µl enzymobeads and 2 mCi $^{125}$I or $^{131}$I (20 µl) followed by 50 µl 2% β-Dglucose. The reaction was gently vortexed and allowed to proceed at room temperature for 25 minutes. The beads were pelleted by ultracentrifugation at 2500 rpm for 5 minutes. The supernatant was extensively dialyzed in 4 liters PBS at 4° C. with changes every 6 hours over a 24-hour period. Greater than 99% of $^{125}$I-MDA2 was precipitated by trichloroacetic acid (TCA) proving the purity of the radiolabel. The specific activity was approximately 3000 cpm/ng. Approximately 90 µCi (50–100 µg) were injected in each experiment. Specificity for MDA-LDL was not affected by radiolabeling as assessed by radioimmunoassay.

Technetium labeling. $^{99m}$Tc-MDA2 was formed by the stannous chloride reduction method which reduces pertechnetate (TcO$_4$) to a lower oxidation state allowing it to covalently bind with free sulfhydryl groups present on the antibody. Addition of sulfhydryl groups to lysine moieties on whole, intact MDA2 was done using a conventional technique. Briefly, 1–2 mg MDA2 was dialyzed in triethanolamine buffer, pH 8.0, overnight at 4° C., harvested and placed on ice in a 0.7 ml microfuge tube. Twenty µl of 2-iminothialane (2-IMT, 0.5M) was added to reach a final concentration of 20 mM and the reaction allowed to proceed for 100 minutes. The solution was placed on a G-25 sephadex column (Pharmacia) equilibrated with degassed tartrate (40 mM)/EDTA(5 mM) buffer at pH 5.6 and the protein fraction collected in the first 4 ml. The solution was concentrated in an Amicon filter at 2000 rpm for 15 minutes to a final volume of 0.5 ml. The protein concentration was determined by both the micro BCA (Pierce) and Biorad methods. The number of sulfhydryl groups added was determined with Ellman's DTNB reagent (Pierce).

Cysteine was used as the standard. Analysis revealed that approximately 25 additional SH groups were added per whole antibody (MDA2-SH).

For technitium labeling all buffers were degassed and argon flushed prior to use. 50 µl stannous chloride (1 M dissolved in 1 N Hcl) was added to 10 ml of pretinning buffer [(tartrate (40 mM), EDTA(4 mM), and ascorbate (30 mM)] and the pH adjusted to 5.6 with iN NaOH. To 100 µg MDA2-SH, (1 mg/ml), in tartrate (40 mM)/EDTA(5 mM) buffer, pH 5.6, was added 100 µl stannous chloride buffer and 15 mCi freshly eluted pertechnetate from a $^{99}$Mo/$^{99m}$Tc generator and the reaction allowed to proceed at room temperature for 1 hour. The solution was placed on a G-25 sephadex column and eluted with tartrate (40 mM)/EDTA(5 mM) buffer. The labeling efficiency was 50–65%. The $^{99m}$Tc-MDA2 came off in the first 4 ml as a single peak and was 90–95% pure by TCA precipitation. PHAST gel (4–15% polyacrylamide gradient) electrophoresis confirmed that the radiolabel co-migrated with the band associated with MDA2. Specificity for MDA-LDL was not affected as assessed by chemiluminescence assay.

Figure 2:
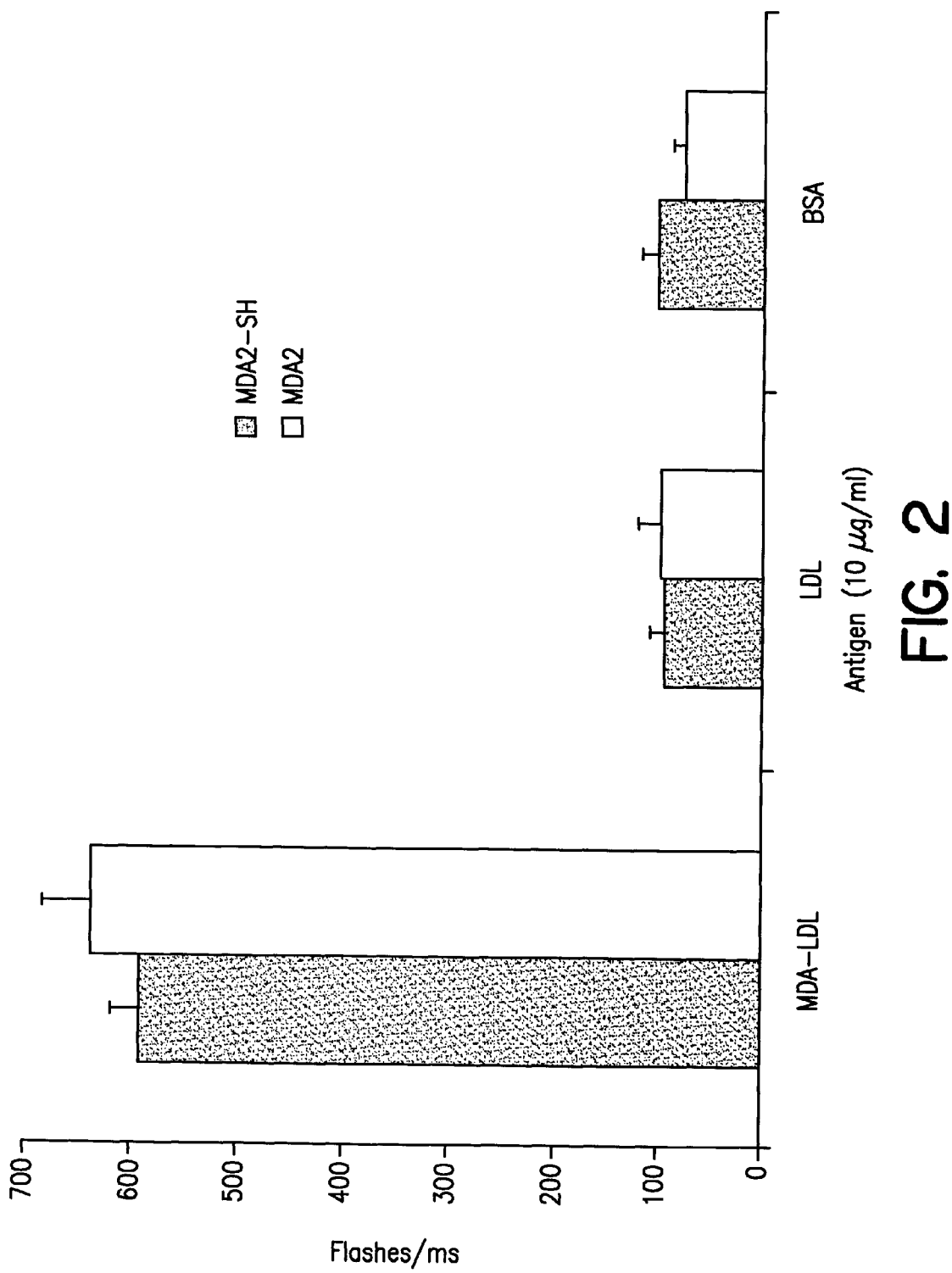
FIG. 2 is a graph of data showing in vitro binding (determined by radioimmunoassay) of technetium labeled MDA2 antibody to MDA-LDL in preference to LDL, demonstrating that binding specificity was not lost by radiolabeling the antibody. Bovine serum albumin (BSA) is the control.

Iodination of MDA2 with the Enzymobead method did not affect its ability to specifically recognize MDA-LDL. FIG. 1 shows that MDA2 has a 11.8 fold higher binding to human MDA-LDL than to LDL or BSA. For technitium labeling, the modification procedure for the addition of SH groups resulted in 20–25 additional SH groups per antibody molecule as determined with Ellman's reagent. FIG. 2 shows by chemiluminescence assay that addition of SH groups to MDA2 did not affect the ability of MDA2-SH to recognize MDA-LDL.

EXAMPLE III

MDA-LDL Synthesis and Modification of LDL and Albumin With Malondialdehyde

LDL was prepared by ultracentrifugation in the presence of antioxidants and protease inhibitors. MDA-LDL was prepared by incubating LDL for 3 hours at 37° C. with 0.5 M malondialdehyde at a constant ratio of 100 µl/mg of LDL. 0.5 M malondialdehyde was freshly generated from malonaldehyde bis dimethylacetal by acid hydrolysis. After conjugation, MDA-LDL was extensively dialyzed against PBS to remove any unreacted MDA. The degree of MDA-modification was determined b conventional trinitrobenzenesulfonic acid assay and averaged 75% of the lysine residues. In addition, the electrophoretic mobility of the modified lipoproteins was compared to that of native LDL by electrophoresis using 1% agarose gels in borate buffer pH 8.6. Albumin was modified with MDA in a similar fashion.

EXAMPLE IV

Animal Model and Protocol

Rabbit model. Seventeen WHHL and 4 NZW rabbits, both on a regular diet, were used for the experiments. The mean age of the WHHL was 1.5±1.0 years and for the NZW 6±0.0 months. Mean weight was 3.1±0.3 kg for all rabbits. WHHL spontaneously develop atherosclerosis without cholesterol feeding and have total cholesterol levels of 800–1200 mg/dl. They develop both coronary and aortic atherosclerosis. In this study we evaluated aortic lesions only. NZW rabbits were atherosclerosis free.

Injection protocol. The rabbits were intravenously injected one hour prior to each experiment with 1 mg/kg sodium iodine to reduce thyroid uptake of the iodinated radiolabel. The radiolabeled antibodies were drawn up into a 1 ml glass syringe without dead volume and direct injections of 0.25–0.5 ml were carried out through a marginal ear vein using a 23 gauge needle. After injection, blood was drawn into the syringe and reinjected several times to insure adequate injection of the entire contents. The contralateral ear was used for blood drawing. Samples of blood were drawn into 3 milliliter tubes containing dry EDTA at 12, 24, 36, 240 and 360 minutes and at 24 hours. For the imaging protocol, a 23 gauge catheter was placed in a marginal ear vein and 5 mCi $^{99m}$Tc-MDA2 in 2 ml tartrate/EDTA buffer was injected followed by a heparinized saline flush.

EXAMPLE V

In vivo Imaging of Atherosclerotic Plaque with MDA2

Imaging protocol. After injecting with $^{99m}$Tc-MDA1 or $^{131}$I-MDA2 the rabbits were anesthetized with xylazine (5 mg/kg) and ketamine (20 mg/kg) intramuscularly and placed supine on the imaging table with their limbs gently extended. Images were carried out for 5–10 minutes at 30 minutes and 20–30 minutes at 24 hours. After the 24 hour image, 10 mg MDA-LDL was given intravenously to clear background as described below in Example VI, and repeat images were carried out at 26 hours. Images were collected with a MEGC gamma camera with a 256X256X16 grid for a total of 1,000,000 counts. The data was analyzed on a SUN Microsystem system.

Results. Four models were used to assess the in vivo uptake and antibody specificity of MDA2 . WHHL were injected with $^{125}$I-MDA2 (WHHL-$^{125}$I-MDA2, n=7) to assess oxidation-specific atherosclerotic plaque uptake and with $^{125}$I-Halb (WHHL-$^{125}$I-Halb, n=4) as the control to assess non-specific uptake. NZW rabbits were also injected with $^{125}$I-MDA2 and $^{125}$I-Halb to assess uptake in normal tissue (NZW-$^{125}$ I-MDA2, n=2 and NZW-$^{125}$I-Halb, n=2).

The diameter of the WHHL aorta is less than one centimeter and its wall thickness varies with the amount of atherosclerosis. Due to the small size of the aorta and interference of closely packed organs such as the kidneys, liver and gut it is challenging to obtain adequate windows for imaging. The arch, where significant amount of plaque exists, is especially difficult in view of the proximity of the heart and lung blood pool. Previous investigators used balloon injury models of the abdominal aorta which is accessible from the anterior-posterior (A-P) and oblique projections. In these experiments WHHL were imaged without balloon injury as their plaques closer resemble human, native atherosclerosis. To ensure that the rabbits had extensive disease down to the abdomen we chose older rabbits (3–4 years old).

Figure 3:
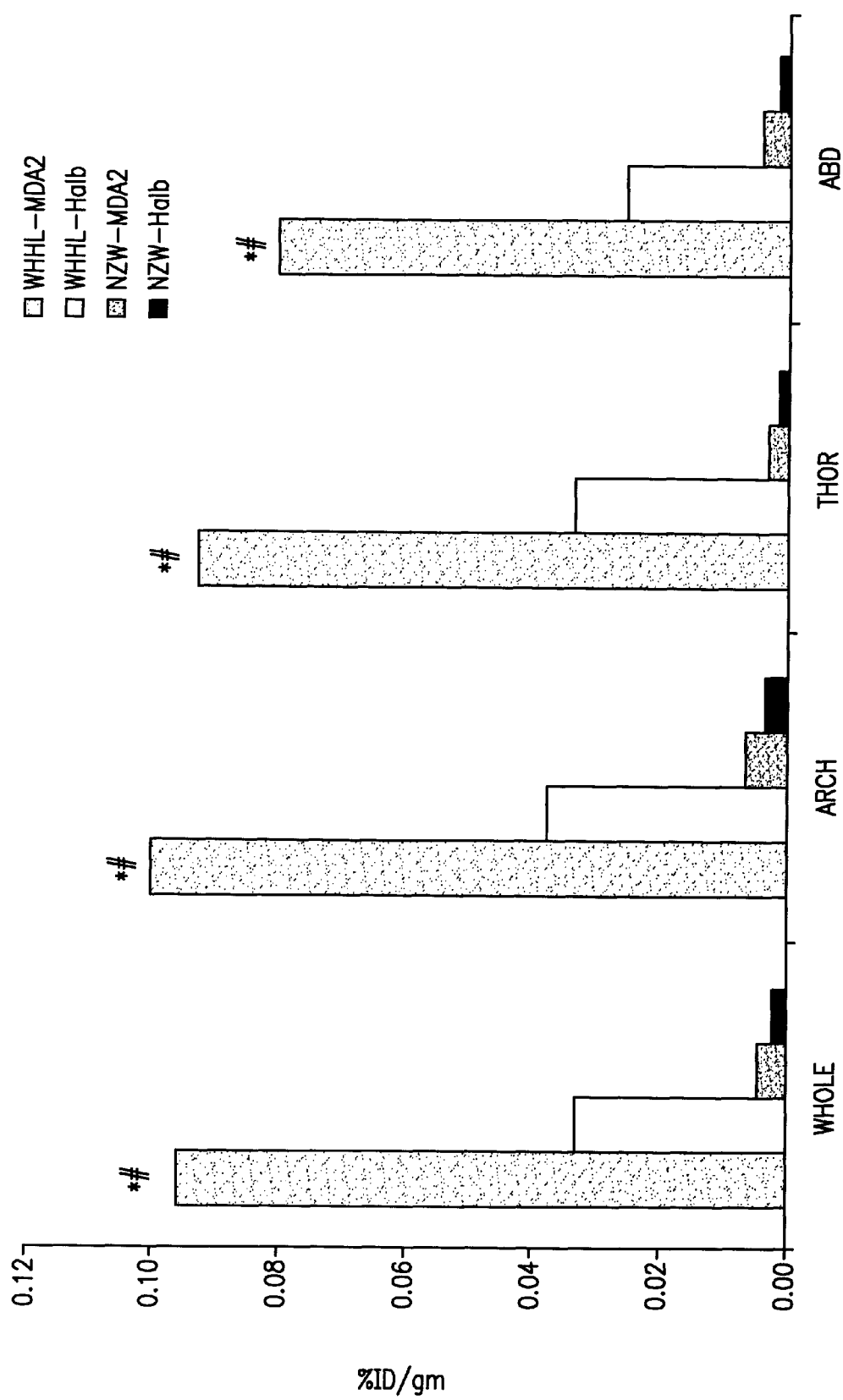
FIG. 3 is a graph of data showing the % ID (injected dose)/gram uptake of radiolabeled (iodinated) MDA2 in tissue segments obtained from animals injected live; i.e., Watanabe Heritable Hyperlipidemic (WHHL) rabbits (models for atherosclerosis) and New Zealand White (NZW) rabbits (healthy controls). Halb (an isotype-matched antibody directed against human albumin) was used as a control.

FIG. 3 represents the in vivo antibody uptake in the whole aorta and in each segment. The uptake of $^{125}$I-MDA2 in the arch plaque of WHHL was 15.2 fold higher than NZW arch (0.100±0.010%ID/gm vs. 0.006±0.003, p=0.00004). This difference was statistically maintained in the thoracic and abdominal segments with 28.4 and 17.9 fold greater uptake respectively, averaging 21.6 for the entire aorta. The higher uptake is directly related to the uptake of $^{125}$I-MDA2 within the atherosclerotic plaque of the WHHL. The uptake of $^{125}$I-Halb WHHL arch plaque (0.100±0.010%ID/gm vs. 0.033±0.003, p=0.0005). Since $^{125}$I-Halb does not recognize rabbit antigens and since the uptake in normal tissue (NZW) is quite low, it is likely that the increased uptake of $^{125}$I-Halb in WHHL plaque reflects a selective permeability and/or retention that is intrinsic to atherosclerotic tissue. The uptake of $^{125}$I-MDA2 and $^{125}$I-Halb in WHHL decreased from arch to abdominal aorta which reflects the greater amount of atherosclerosis in the proximal aorta in the WHHL. There was very low uptake of $^{125}$I-MDA2 and $^{125}$I-Halb in NZW whole aorta (uptake was 0.004±0.002%ID/gm vs. 0.002±:0.001, respectively, P=0.43).

Figure 4:
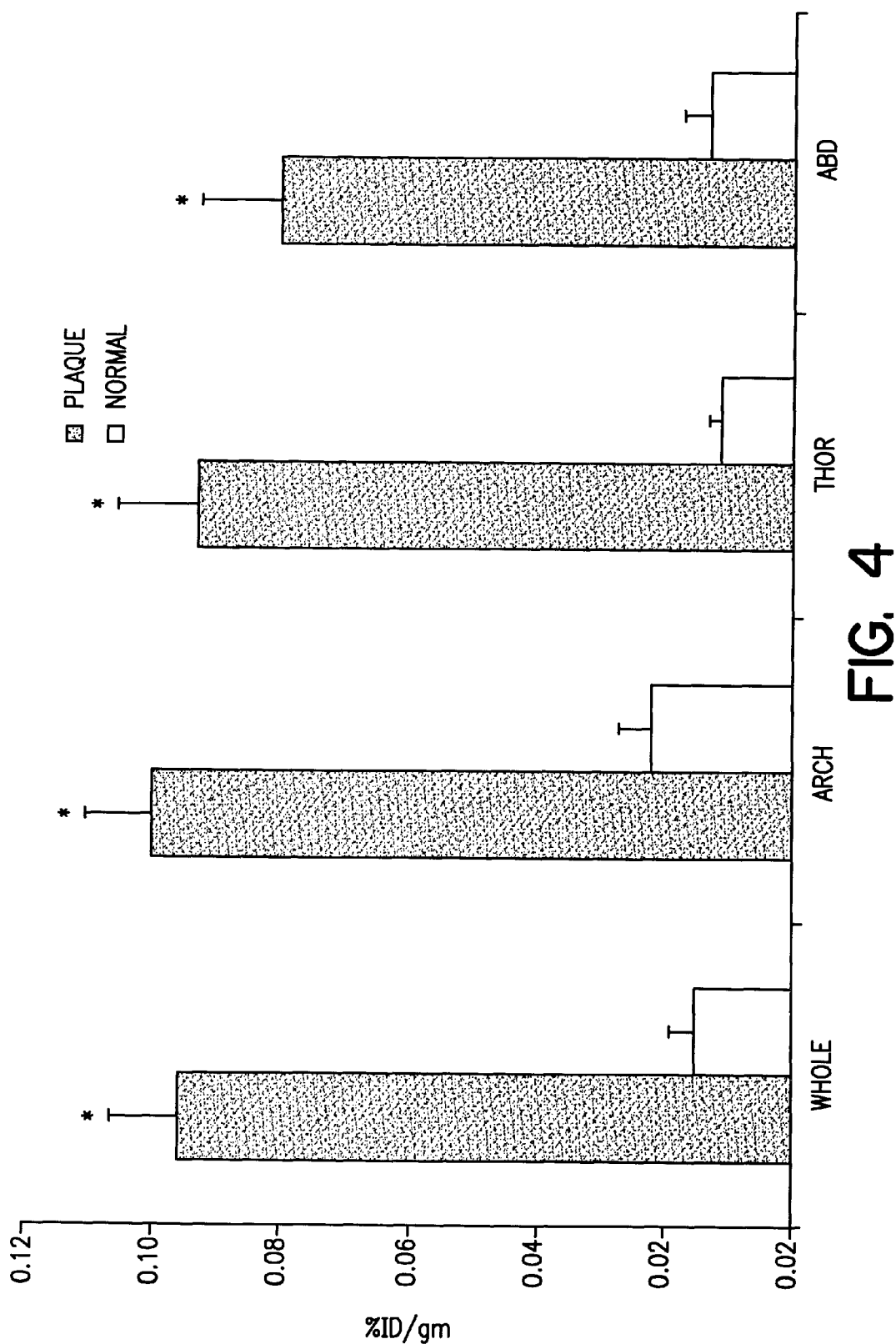
FIG. 4 is a graph of data showing iodinated MDA2 uptake (%ID/gram) in WHHL rabbit aortic plaque versus adjacent normal tissue uptake.

The specificity of $^{125}$I-MDA2 for atherosclerotic tissue can also be further appreciated in FIG. 4 which examines the relationship of MDA2 uptake in plaque versus adjacent grossly normal tissue in WHHL rabbits. When the uptake of MDA2 in plaque, compared to adjacent grossly normal arterial tissue, was expressed as the ratio of %ID/gm plaque divided by %ID/gm adjacent tissue, a mean of 8.5 was found in the whole aorta, 5.3 in the arch, 8.5 in the thoracic aorta, and 9.8 in the abdominal aorta. The uptake of $^{125}$I-MDA2 in grossly normal areas in WHHL aortas is higher than in normal arterial tissue in NZW rabbits due to the fact that WHHL rabbits have intimal thickening and interspersed foam cells in areas that appear normal grossly. These very early areas of atherosclerosis are greater in the arch vs. thoracic vs. abdominal such that the latter take up MDA2 less strongly. When comparing the arch plaque in WHHL versus the grossly normal areas in the abdominal aorta which are the least affected by atherosclerosis in the same rabbits the ratio increases to 12.6 which is similar to the ratio of WHHL versus NZW.

EXAMPLE VI

Elimination of Background Radioactivity

Figure 5:
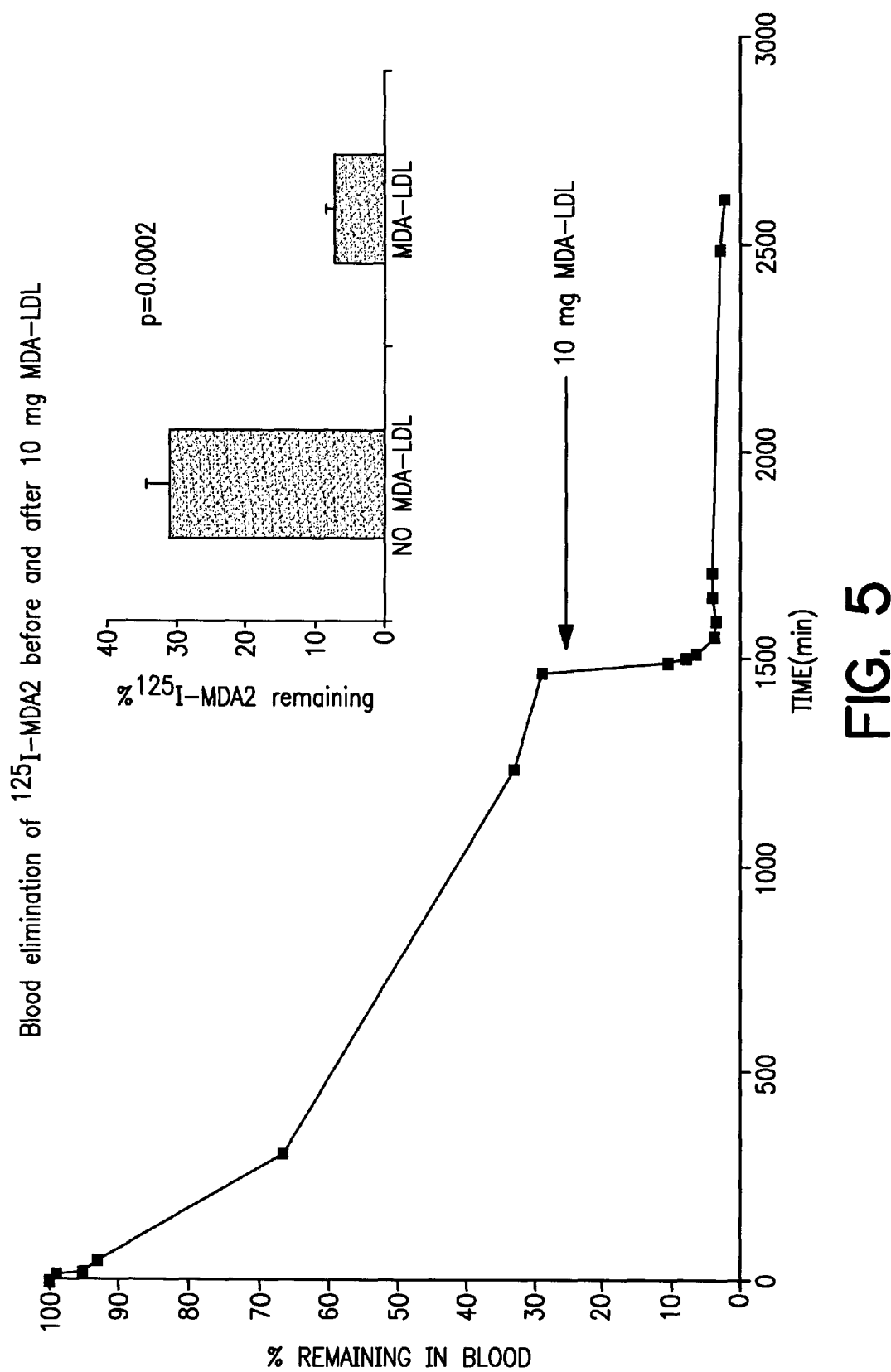
FIG. 5 is a graph comparing elimination rates for iodinated MDA2 from blood before and after injection of 10 mg MDA-LDL antigen joined to albumin as a carrier. The insert describes the differences in remaining radioactivity after 24 and 26 hours (31% and 7%, respectively) following injection of the MDA-LDL antigen.
Figure 9:
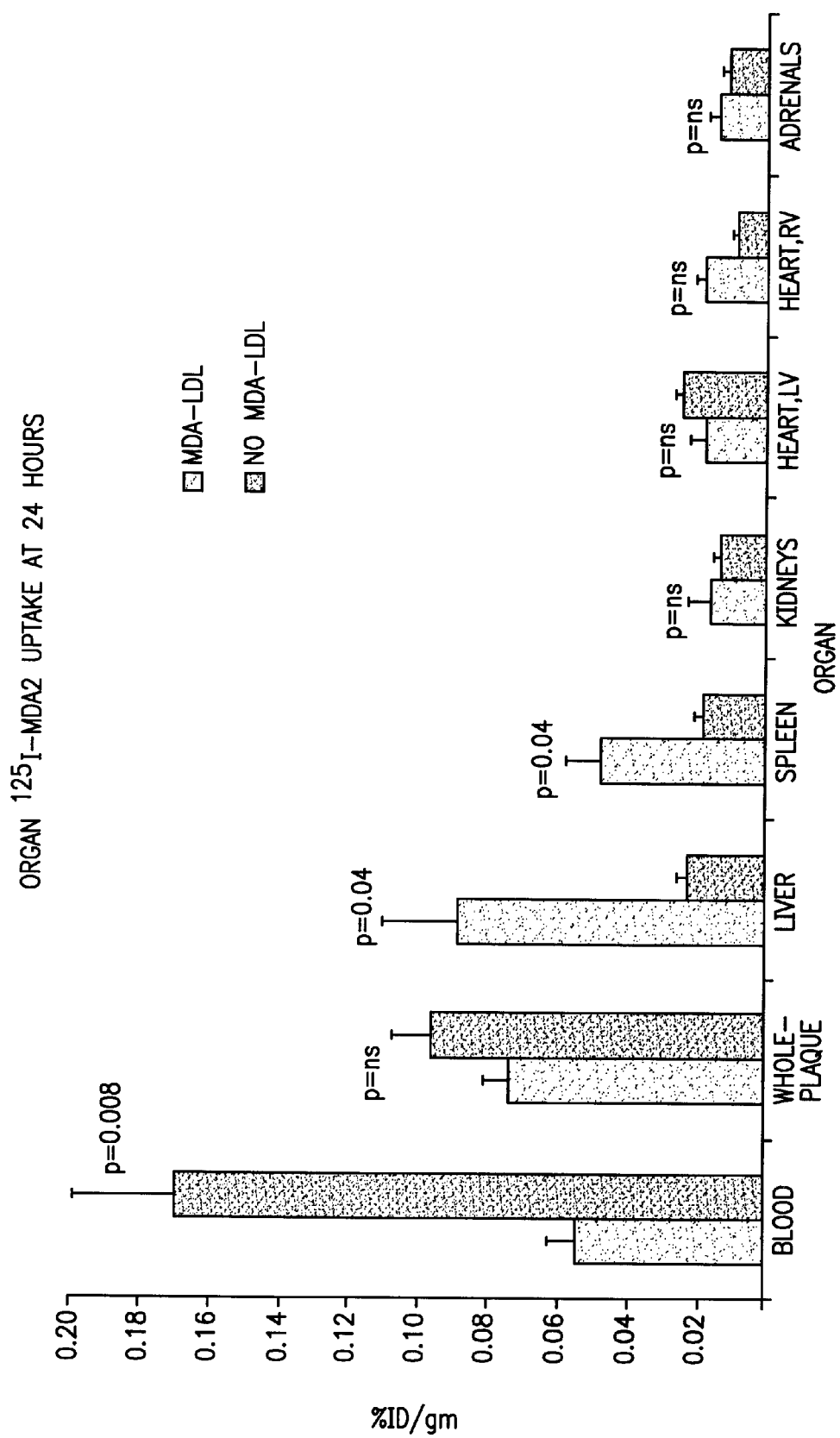
FIG. 9 is a graph of data showing the tissue distribution of MDA2 antibody before and after injection of MDA-LDL antigen to clear residual blood radioactivity.

Antibody Uptake. By injecting the antigen of MDA2, MDA-LDL, antigen/antibody complexes are formed and eliminated from the circulation by the reticuloendothelial system. After several pilot experiments a dose of 10 mg MDA-LDL (75% modification of lysine residues by malondialdehyde) was used. A typical example is shown in FIG. 5 which reveals the plasma decay of $^{125}$I-MDA2 in a WHHL before and after intravenous injection of 10 mg MDA-LDL. Following documentation of this effect a second group of 5 WHHL were injected with MDA2 as described previously and at 24 hours 10 mg MDA-LDL were injected to remove residual plasma of $^{125}$I-MDA2. The rabbits were sacrificed at a mean of 2 hours post injection and the MDA2 uptake determined. The results are shown in the insert in FIG. 5 and are compared to the uptake in the previous group of 7 WHHL rabbits receiving MDA2. The remaining blood radioactivity was reduced from 31±3.3% to 7.3±1.2% (p=0.0002). The $^{125}$I-MDA2 leaving the circulation was sequestered in the liver and spleen as shown in FIG. 9. The residual $^{125}$I-MDA2 in the blood was approximately 50% intact and 50% free iodine as assessed by TCA precipitation assay suggesting that there was significant cleavage and release of $^{125}$I once the intact radiolabeled MDA2 entered the reticuloendothelial system. There was negligible free iodine in the circulation in the 24 hours prior to injection of MDA-LDL.

Figure 6:
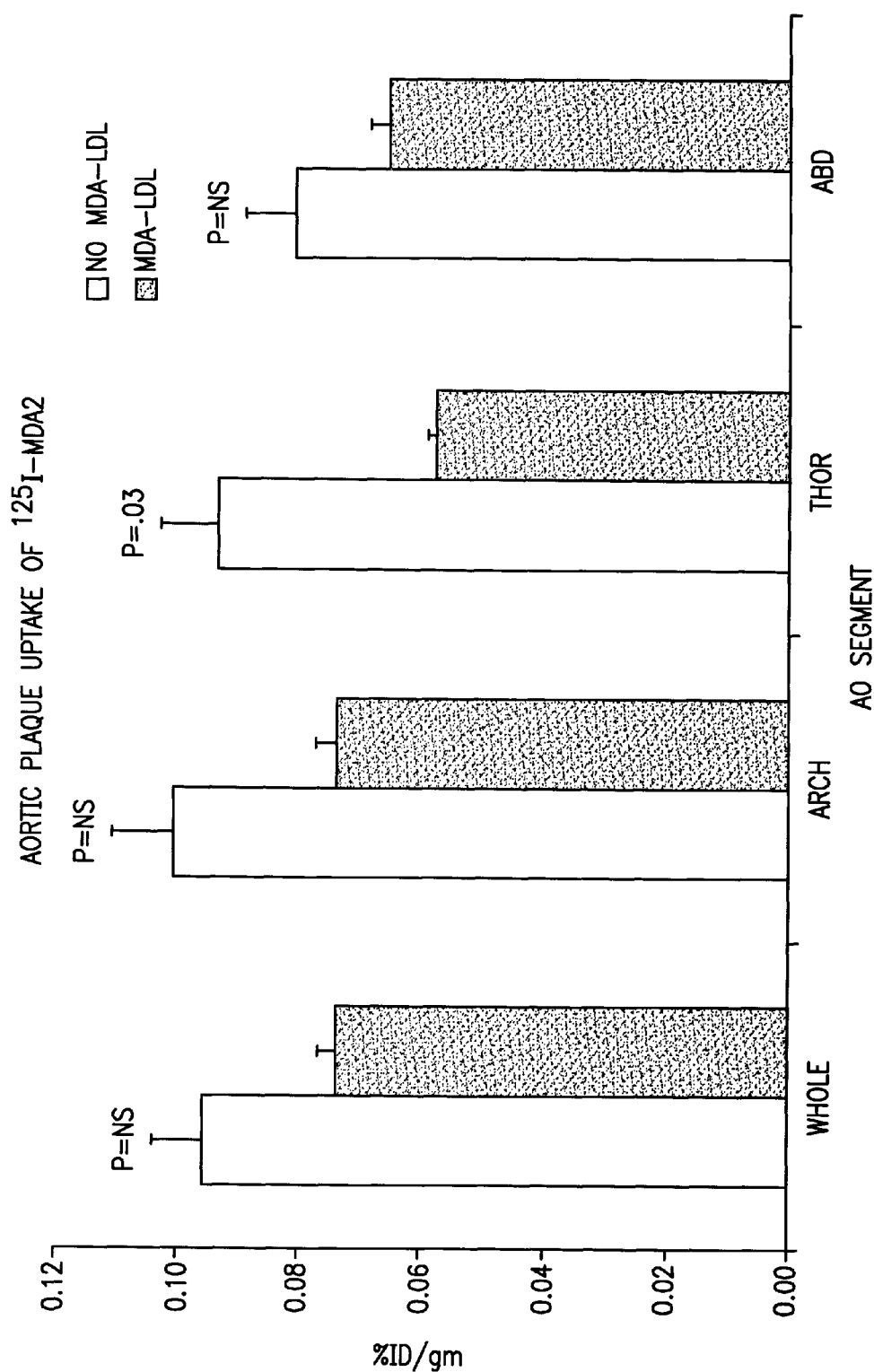
FIG. 6 is a graph of data showing that uptake of MDA2 antibody in WHHL rabbit plaque is relatively unaffected by post-antibody injection of MDA-LDL antigen to clear residual radioactivity in blood.

As shown in FIG. 6, uptake of MDA2 was relatively unaffected by injection of MDA-LDL.

Figure 7:
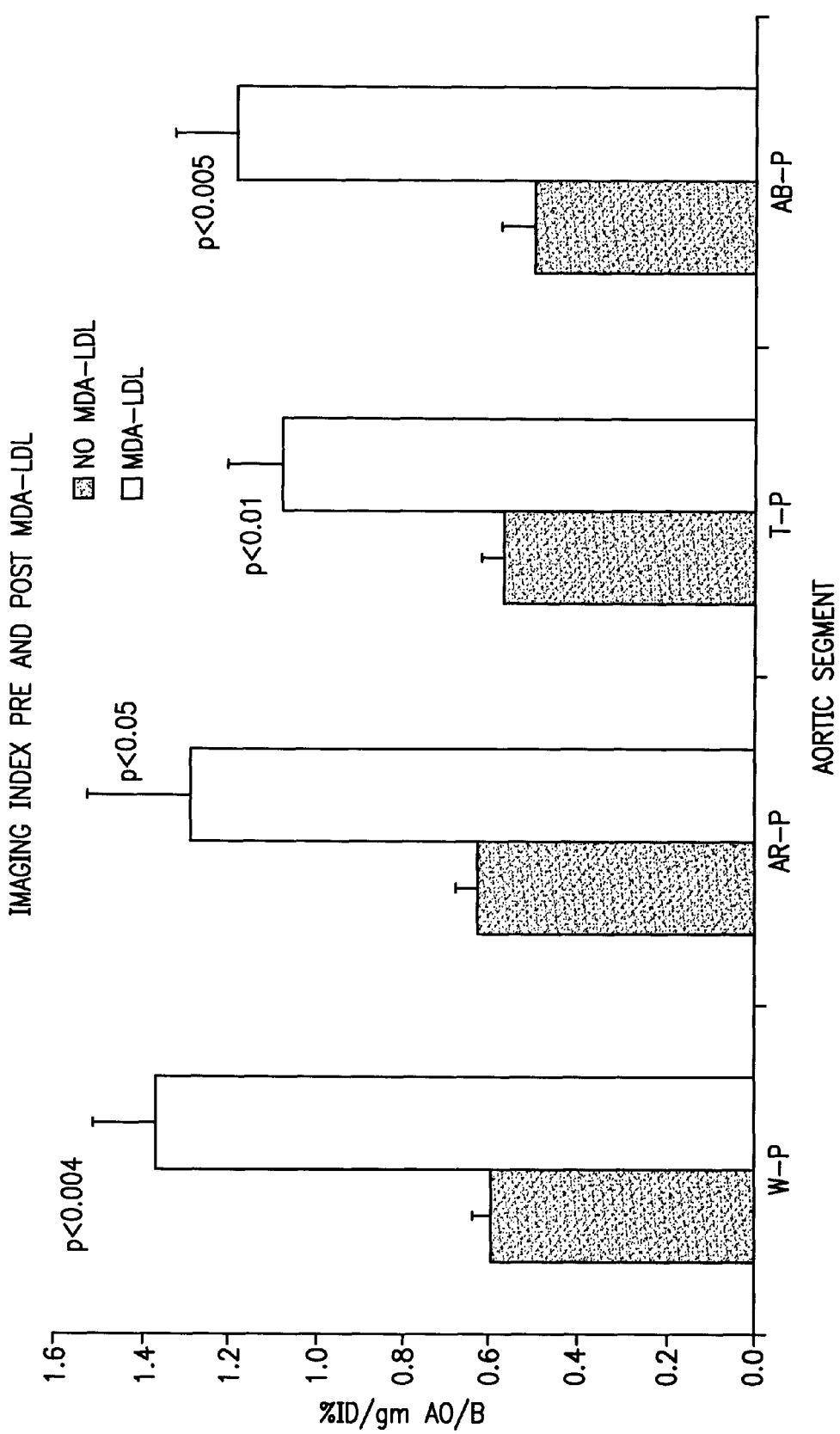
FIG. 7 is a graph of data showing the improvement in the imaging ratio (target-to-background) for MDA2 24 hours before and after injection of MDA-LDL antigen to clear residual radioactivity in blood.

Imaging index. The ability to derive images of an object with nuclear scintigraphy techniques requires high uptake of radiolabel in the target and low background signal at a time when the signal is strongest in the area of interest. This target to background ratio can e expressed by an imaging index defined as the ratio of the %ID/gm uptake in plaque versus %ID/gm in blood. On a theoretical basis any ratio over one can provide resolution of the target if the radiolabel signal is strong enough to be detected. On a practical basis for atherosclerosis imaging in arteries, the imaging index must be higher due to the geometry and size of the vessel and the blood in the lumen and the plaque dimensions. FIG. 7 describes the improvement in the imaging ratio in the WHHL rabbits imaged as described above after removal of radiolabel from the circulation. In the arch the radio increased from 0.6±0.05 to 1.3±0.24 (p=0.004). Improvement in the imaging index was noted in all areas of the aorta.

EXAMPLE VII

Figure 8A:
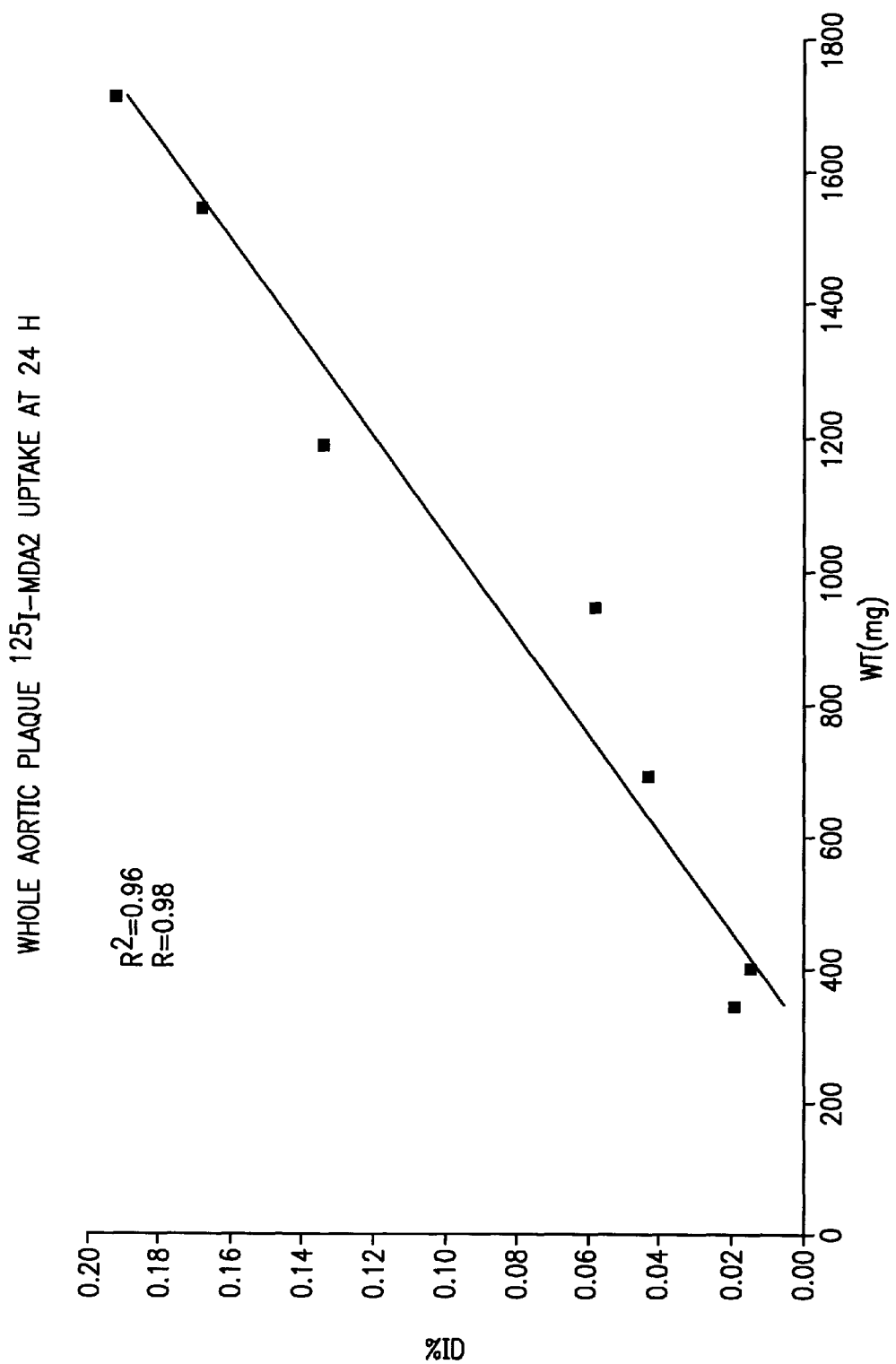
FIG. 8a is a graph of data showing the relationship between MDA2 antibody uptake in plaque and aortic weight solely as a function of injected dose (%ID).
Figure 8B:
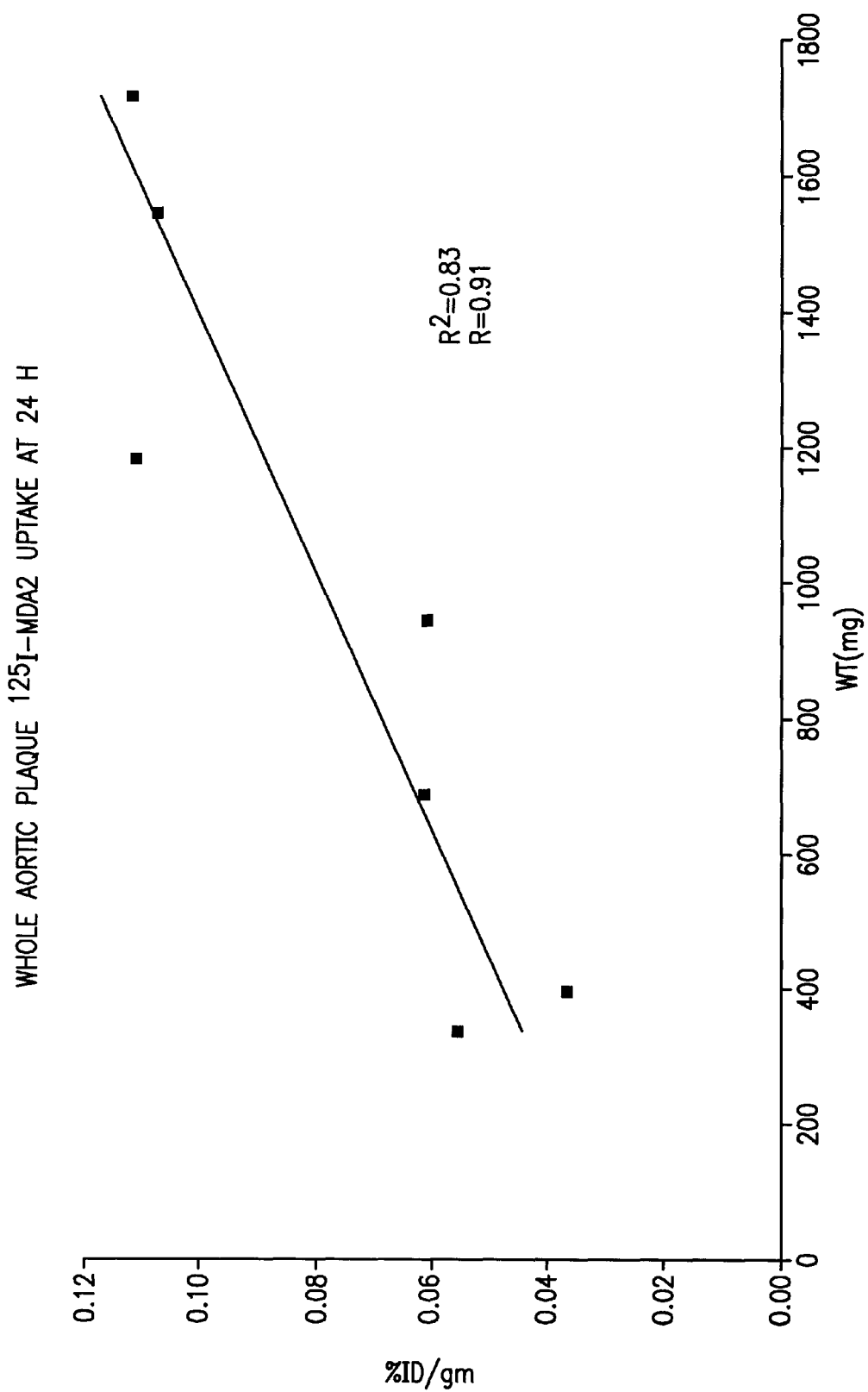
FIG. 8b is a graph of data showing the relationship between MDA2 antibody uptake in plaque and aortic weight as a finction of injected dose (%ID)/gram body weight (normalized to weight).

Correlation Between Percent Injected Dose (%ID) Uptake and Aortic Weight (Atherosclerosis) in WHHL Aortic weight increases linearly as atherosclerosis progresses due to increasing plaque surface area and plaque volume; these factors correlate to MDA2 uptake in WHHL. WHHL rabbits have variable expression of atherosclerosis even in similar age groups. This group of rabbits receiving $^{125}$I-MDA2 (n=7) had 40–95% surface area atherosclerosis which allowed examination of differential uptake. Since $^{125}$I-MDA2 uptake is compared in FIGS. 8a and 8b in the same group of rabbits, the %ID may be studied without normalizing to weight. There was a very strong correlation (r=0.98) between the %ID uptake in the entire plaque of the aorta versus the entire aortic weight (FIG. 8a). There was also a good correlation between the %ID/gm vs. weight (normalizing for the weight) which suggests that as the plaques enlarge, $^{125}$I-MDA2 recognizes more oxidation epitopes per unit weight, i.e., the plaque per unit density contains more oxidation specific epitopes (FIG. 8b). In advanced atherosclerosis there would be less correlation between aortic area atherosclerosis and weight since in advanced atherosclerosis, the plaque grows by thickening which would not be detected by a surface area calculation.

EXAMPLE VIII

Tissue and Blood Uptake and Clearance of Antibody

FIG. 9 describes the tissue uptake before and after injection of MDA-LDL. At 24 hours the blood has the highest amount of radiolabel followed by the aortic plaque. Following MDA-LDL the circulating $^{125}$I-MDA2 has been removed and taken up by the liver and spleen within the next two hours. At this point the highest uptake is within the liver followed by the aortic plaque. Most of the $^{125}$I-MDA2 ends up in the liver before and after MDA-LDL.

The invention having been fully described, modifications to the methods and reagents of the invention may be apparent to those of ordinary skill in the art. All such modifications are within the scope of the invention.

The invention claimed is:

1. A method of imaging atherosclerotic plaque in a host, comprising:
   (a) introducing a diagnostically effective amount of detectably labeled monoclonal antibody or fragment thereof into the cardiovascular tissue of the host, wherein the monoclonal antibody is specific for oxidation specific epitopes bound by MDA2 and NA59 in plaque and binds such epitopes in vivo at a rate of about ten to twenty times the rate of binding of the monoclonal antibody to normal arterial tissue;
   (b) reducing residual radioactivity in the host by introducing a sufficient amount of an antigen, specific for the detectably labeled monoclonal antibody, into the host to bind any detectably labeled monoclonal antibody unbound following its introduction in step (a); and,
   (c) determining whether the monoclonal antibody has bound oxidized LDL, wherein binding of said antibody in cardiovascular tissue is indicative of the presence in such tissue of atherosclerotic plaque.

2. The method of claim 1, wherein the detectably labeled monoclonal antibody is MDA2.

3. The method of claim 2, wherein the MDA2 antibody is a chimeric antibody.

4. The method of claim 1, wherein the detectably labeled monoclonal antibody is NA59.

5. The method of claim 4, wherein the NA59 antibody is a chimeric antibody.

6. The method of claim 1, wherein the weight of any atherosclerotic plaque detected in the cardiovascular tissue is estimated as a correlate of the percent injected dose of detectably labeled monoclonal antibody/gram of host body weight.

7. The method of claim 1, wherein the detectable label is selected from the group consisting of a radioisotope and a paramagnetic label.

8. A kit for use in imaging atherosclerotic plaque in a host comprising:
   a) a detectably labeled monoclonal antibody or fragment thereof which is specific for oxidation specific in plaque which are bound by MDA2 and NA59 and binds such epitopes in vivo at a rate of about ten to twenty times the rate of binding of the monoclonal antibody to normal arterial tissue, wherein the monoclonal antibody is in a pharmaceutically acceptable carrier;
   b) a container containing the detectably labeled monoclonal antibody; and
   c) instructions for use of the detectably labeled monoclonal antibody for use in imaging atherosclerotic plaque in a host.

9. The kit according to claim 8, wherein the detectably labeled monoclonal antibody is MDA2.

10. The kit according to claim 9, wherein the MDA2 antibody is a chimeric antibody.

11. The kit according to claim 8, wherein the detectably labeled antibody is NA59.

12. The kit according to claim 11, wherein the NA59 antibody is a chimeric antibody.

* * * * *